United States Patent [19]

Kitahata et al.

[11] Patent Number: 5,393,660
[45] Date of Patent: Feb. 28, 1995

[54] REAGENT FOR DETERMINING α-AMYLASE ACTIVITY AND METHOD FOR DETERMINING α-AMYLASE ACTIVITY

[75] Inventors: Sumio Kitahata, Osaka; Nobuhiro Kuwahara, Yokohama; Koki Fujita, Yokohama; Koji Hara, Yokohama; Keiichi Majima, Tsuruga; Shin-ichi Teshima, both of Tsuruga; Yuzo Hayashi, Osaka, all of Japan

[73] Assignees: Toyo Boseki Kabushiki Kaisha, Osaka; Ensuiko Sugar Refining Co., Ltd., Kanagawa, both of Japan

[21] Appl. No.: 147,717

[22] Filed: Nov. 4, 1993

[30] Foreign Application Priority Data

Nov. 10, 1992 [JP] Japan .................... 4-300103

[51] Int. Cl.[6] .................... C12Q 1/40; C12N 9/26
[52] U.S. Cl. .................... 435/22; 435/201
[58] Field of Search .................... 424/7.1, 94.1, 94.6, 424/94.61; 435/22, 202, 203, 204, 201

[56] References Cited

U.S. PATENT DOCUMENTS

5,158,872  10/1992  Chavez .................... 435/22

FOREIGN PATENT DOCUMENTS

0078994  5/1985  Japan .
3214193  9/1988  Japan .
3-264596  11/1991  Japan .
5208989  8/1993  Japan .

OTHER PUBLICATIONS

*Nippon Nogeikagaki Kaisha*, vol. 65, No. 3, p. 117, dated Mar. 15, 1991 and English Summary.
Ogawa et al., "Differential Assay of Human Pancreatic & Salivary α-Amylase w/p-Nitrophenyl $6^5$-O-β-D-Galacopyrasoyl-α-maltopentaoside as the Substrate", Biosci., Biotech. Biochem. 56(12) 1933-1936, 1992.
Ishimaru et al., "Enzymatic Synthesis of 2—Chloro-4-nitrophenyl 4,6-O-3-Ketobutylidene β-Maltopentaoside, a Substrate for α-Amylase", Biosci., Biotech., Biochem. 56(10), 1552-1556, 1992.

*Primary Examiner*—Jeffrey E. Russel
*Assistant Examiner*—Nancy J. Gromet
*Attorney, Agent, or Firm*—Leydig, Voit & Mayer, Ltd.

[57] ABSTRACT

A reagent for determining α-amylase activity, comprising a maltooligosaccharide derivative of the following formula

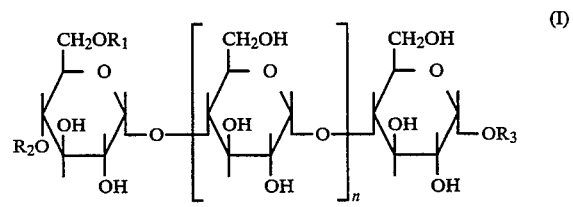

(I)

(wherein either one of $R_1$ and $R_2$ is β-galactopyranosil and the other is hydrogen, $R_3$ is a group bonded to the reducing terminal glucose via a bond cleavable by α-amylase, which becomes a measurable substance upon cleavage of the bond, and n is an integer of 0–2), which does not comprise adjuvant enzymes; and a method for determining α-amylase activity which comprises use of the reagent. The reagent of the present invention does not require use of any adjuvant enzyme and is stable since the substrate is not exposed to the decomposition by an adjuvant enzyme. The substrate used in the present invention has high affinity for α-amylase. Thus, the reagent and the determination method of the present invention make it possible to determine α-amylase activity with high sensitivity.

15 Claims, No Drawings

REAGENT FOR DETERMINING α-AMYLASE ACTIVITY AND METHOD FOR DETERMINING α-AMYLASE ACTIVITY

The present invention relates to a novel reagent for determining α-amylase activity and to a novel method for determining α-amylase activity. More specifically, the present invention relates to a reagent for determining α-amylase activity, containing, as a substrate, a maltooligosaccharide derivative having 2–4 glucose units and a β-galactopyranosyl group at the 4- or 6-position of non-reducing terminal glucose, which does not contain adjuvant enzyme; and to a method for determining α-amylase activity, which comprises use of said reagent.

Various diseases have been conventionally diagnosed by determining the activity of α-amylase in a body fluid such as pancreatic juice and urine. The methods for determining α-amylase activity are exemplified by the following.

(1) A method using a maltooligosaccharide (e.g. maltotetraose, maltopentaose, maltohexaose) as a substrate, According to this method, said maltooligosaccharide and an adjuvant enzyme such as a-glucosidase are allowed to react with a sample containing α-amylase to liberate glucose from the substrate, and α-amylase activity is determined by measuring the amount of the liberated glucose. The methods for measuring the liberated glucose include, for example, a method using glucose oxidase/peroxidase/indicator system, a method using hexokinase/glucose-6-phosphate dehydrogenase system, and a method utilizing hexokinase/phosphoglucomutase/glucose-6-phosphate dehydrogenase/NADH system. However, a reagent containing α-glucosidase and a substrate in one container shows poor stability, since α-glucosidase slightly reacts with the substrate to cause an increased blank value.

(2) A method using a derivative having phenyl, naphthyl, or their derivative bonded as an aglycone to the reducing terminal of maltooligosaccharide.

According to this method, said maltooligosaccharide derivative and an adjuvant enzyme such as α-glucosidase are allowed to react with a sample containing α-amylase to liberate aglycone from the substrate, and α-amylase activity is determined by optically measuring the liberated aglycone.

Examples of the substrate used in this method include p-nitrophenyl maltopentaoside, p-nitrophenyl maltohexaoside, p-nitrophenyl maltoheptaoside, 2,4-dichlorophenyl maltopentaoside, and 2-chloro-4-nitrophenyl maltopentaoside.

This method is also subject to the aforementioned disadvantage that α-glucosidase slightly reacts with the substrate to cause an increased blank value. A reagent containing α-amylase and a substrate in one container is undesirable, since it is susceptible to the degradation of stability of the reagent, because of the activity of α-amylase to break down the substrate.

In addition, the both methods (1) and (2) require use of adjuvant enzyme, thereby rendering the production cost high.

(3) A method using, as a substrate, a maltooligosaccharide derivative wherein the hydroxyl group(s) at the 4- and/or 6-position(s) of the non-reducing terminal glucose thereof are(is) substituted by (a) substituent(s) and the reducing terminal thereof is bonded with phenyl, naphthyl, or their derivative as an aglycone According to this method, said maltooligosaccharide derivative and an adjuvant enzyme such as α-glucosidase are allowed to react with a sample containing α-amylase to liberate aglycone from the substrate, and α-amylase activity is determined by optically measuring the liberated aglycone as in (2).

Specific examples of the substrate include a substrate wherein the hydroxyl group at the 6-position of the non-reducing terminal glucose has been substituted by, for example, halogen or a glucopyranosyl group (Japanese Patent Unexamined Publication No. 237998/1985), a substrate wherein the hydroxyl groups at the 4- and 6-positions have been substituted by alkyl, alkoyl, or phenyl (U.S. Pat. Nos. 4709020, 4818692, 4987067), and a substrate having 4–7 glucose units wherein the hydroxyl group at the 4- or 6-position has been blocked by β-galactopyranosyl group (Japanese Patent Unexamined Publication No. 264596/1991). The aforementioned disadvantage in methods (1) and (2) that α-glucosidase slightly reacts with the substrate to cause an increased blank value has been theoretically overcome, since the hydroxyl group at the 4- or 6-position of the non-reducing terminal glucose of maltooligosaccharide has been blocked. In practice, however, these substrates are still susceptible to a certain degree of increase in blank value due to the decomposition by α-glucosidase, since impurities having an unblocked non-reducing terminal are contained in small amounts. The method (3) also results in high production costs from the use of adjuvant enzyme.

(4) A method using 2-chloro-4-nitrophenyl maltotrioside as a substrate (U.S. Pat. Nos. 4,963,479, 5,158,872)

This method does not require adjuvant enzyme, and is economical. It shows less increase in blank value. Yet, the sensitivity is poor.

Accordingly, the present invention aims at solving the defects of the conventional substrates for the determination of α-amylase activity and the defects of the conventional reagents for the determination of α-amylase activity. An object of the invention is to provide a highly sensitive reagent for the determination of α-amylase activity, the reagent exhibiting high affinity for α-amylase and requiring no adjuvant enzyme, thereby rendering the production cost low and stability of the reagent superior due to the void decomposition of the substrate by adjuvant enzyme.

Another object of the invention is to provide a method for determining α-amylase activity with high sensitivity, which requires no adjuvant enzymes.

The present invention relates to a reagent for determining α-amylase activity, comprising a maltooligosaccharide derivative of the following formula

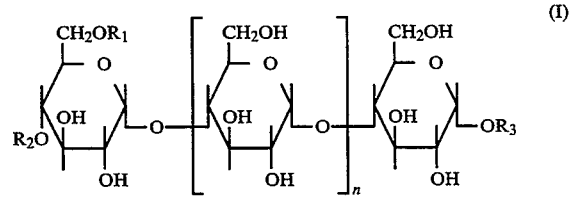

(I)

(wherein either one of $R_1$ and $R_2$ is β-galactopyranosyl and the other is hydrogen, $R_3$ is a group bonded to the reducing terminal glucose via a bond cleavable by α- amylase, which becomes a measurable substance upon cleavage of said bond, and n is an integer of 0-2), which does not comprise adjuvant enzymes.

The present invention also relates to a method for determining α-amylase activity in a sample, which comprises the steps of
(a) contacting the sample with a maltooligosaccharide derivative of the formula

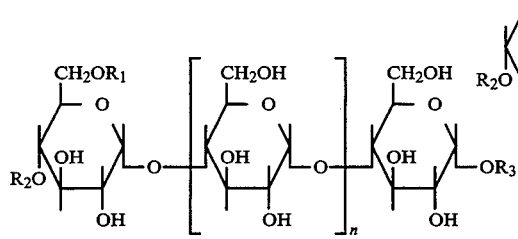
(I)

(wherein either one of $R_1$ and $R_2$ is β-galactopyranosyl and the other is hydrogen, $R_3$ is a group bonded to the reducing terminal glucose via a bond cleavable by α-amylase, which becomes a measurable substance upon cleavage of the bond, and n is an integer of 0-2), in the absence of adjuvant enzyme to cause reaction of the maltooligosaccharide derivative with α-amylase; and (b) measuring the amount of the liberated measurable substance.

The maltooligosaccharide portion of the maltooligosaccharide derivative (I) in the present invention consists of 2-4 glucose units. Specific examples thereof include maltose, maltotriose, and maltotetraose. In particular, compounds having 2 glucose units (n=0) are preferable.

The galactopyranosyl (which is a modifying group for the non-reducing terminal glucose of maltooligosaccharide) represented by $R_1$ or $R_2$ is bonded to the 4- or 6-position hydroxyl of the non-reducing terminal glucose via a β-linkage. Examples of the substrates whose 4- or 6-position of the non-reducing terminal glucose has been modified include those whose 6-position hydroxyl has been substituted by glucopyranosyl, and those whose 4- or 6-position hydroxyl has been substituted by alkyl, alkoyl, or phenyl. These modified substrates are not found among natural substrates. The galactopyranosyl is superior to the aforementioned modifying groups in terms of affinity for α-amylase.

The reducing terminal of maltooligosaccharide has a group $R_3$ which is bonded to the reducing terminal glucose via a bond cleavable by α-amylase and which becomes a measurable substance upon cleavage of said bond ($R_3$ is hereinafter also referred to as aglycone). $R_3$ is bonded to the hydroxyl at the 1-position of the reducing terminal glucose via an α-glycoside linkage. Examples of the group represented by $R_3$ include phenyl residues having substituents such as nitro and halogen (e.g. p-nitrophenyl, o-nitrophenyl, 2-chloro-4-nitrophenyl, 2,4-dichlorophenyl) and luminescent groups such as 4-methylumbelliferyl residue. Of these, 2-chloro-4-nitrophenyl residue is superior in terms of measurement sensitivity at around pH 7 which is the optimal pH for α-amylase. The maltooligosaccharide derivative of the formula (I) which is to be used in the present invention is exemplified by the compounds of the formula

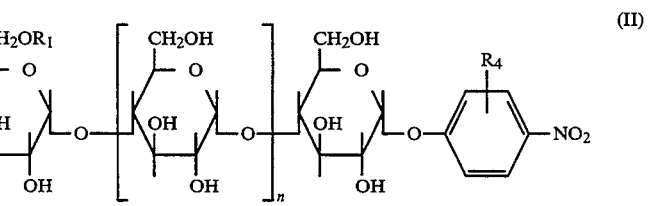
(II)

wherein $R_1$, $R_2$, and n are as defined above, and $R_4$ is hydrogen or a substituent selected from the group consisting of halogen, alkyl residue having 1 to 6 carbon atoms, —$OR_5$, and —$COOR_5$ ($R_5$ is alkyl residue having 1 to 6 carbon atoms).

In the present specification, halogen means fluorine atom, chlorine atom, bromine atom, or iodine atom. Alkyl residue may be a straight or branched one and is exemplified by methyl, ethyl, propyl, isopropyl, butyl, isobutyl, tert-butyl, pentyl, or hexyl, with preference given to those having 1 to 4 carbon atoms.

Examples of the maltooligosaccharide derivative of the formula (I) include 2-chloro-4-nitrophenyl 4-O-β-D-galactopyranosyl-α-maltoside, p-nitrophenyl 4-O-β-D-galactopyranosyl-α-maltoside, 2-chloro-4-nitrophenyl 4-O-β-D-galactopyranosyl-α-maltotrioside, p-nitrophenyl 4-O-β-D-galactopyranosyl-α-maltotrioside, 2-chloro-4-nitrophenyl 4-O-β-D-galactopyranosyl-α-maltotetraoside, and p-nitrophenyl 4-0-β-D-galactopyranosyl-α-maltotetraoside. Preferred are maltooligosaccharide derivatives having 2 glucose units (n=0), and particularly preferred is 2-chloro-4-nitrophenyl 4-O-β-D-galactopyranosyl-α-maltoside.

The maltooligosaccharide derivative (I) to be used in the present invention can be prepared according to known methods such as a method disclosed in Japanese Unexamined Patent Publication No. 264596/1991. The maltooligosaccharide derivative (I) can be prepared, for example, by reacting a maltooligosaccharide derivative (III) having 2-chloro-4-nitrophenyl group bonded at the reducing terminal glucose, which is represented by the formula

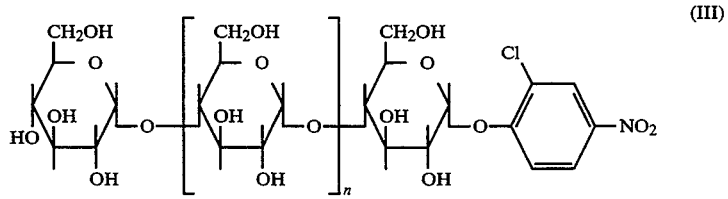
(III)

wherein n is an integer of 0-2, with lactose in the presence of β-galactosidase whereby to introduce β-galactopyranosyl group at the non-reducing terminal of the maltooligosaccharide derivative (III).

Alternatively, a galactopyranosyl maltooligosaccharide derivative may be prepared as follows. A maltooligosaccharide such as maltose, maltotriose, or maltotetraose is allowed to react with lactose in the presence of β-galactosidase whereby to introduce β-galactopyranosyl at the non-reducing terminal of the maltooligosaccharide to give a galactopyranosyl maltooligosaccharide. Then, the galactopyranosyl maltooligosaccharide is acetylated in acetic arthydride in the presence of a base catalyst (e.g. pyridine, sodium acetate) at room temperature or under heating. Thereafter, the resulting acetylated compound is heated in the presence or absence of an inorganic solvent together with alkali, acetic anhydride, and phenol such as 2-chloro-4-nitrophenol to introduce phenyl group to the reducing terminal, after which the thus-obtained compound is subjected to a known deacetylation reaction in methanol with the use of a catalytic amount of sodium methylate.

The reagent for determining α-amylase activity of the present invention contains the above-mentioned maltooligosaccharide derivative (I) as a substrate, and is characterized by the absence of adjuvant enzyme. In the present invention, the adjuvant enzyme is exoglucosidase which hydrolyzes glucoside bond from the non-reducing terminal, and is exemplified by α-glucosidase or glucoamylase, or which hydrolyzes the bond between the reducing terminal glucose and the measurable substance thereof and is exemplified by α-glucosidase or β-glucosidase. The reagent for determining α-amylase activity of the present invention may contain other additives as necessary. Examples of the additives include surfactants, stabilizers, preservatives, and chelating agents.

The reagent of the present invention may further comprise buffers. Examples of the buffer include Good buffers such as PIPES buffer and various buffers exhibiting buffer capacity at around pH 7.0.

The method for determining α-amylase activity of the present invention comprises the steps of (1) contacting a sample containing α-amylase with the aforementioned maltooligosaccharide derivative (I) in the absence of adjuvant enzyme to allow reaction between the maltooligosaccharide derivative and α-amylase; and (2) measuring the liberated measurable substance.

The reaction of maltooligosaccharide derivative and α-amylase proceeds under the same conditions as those for conventional determination of α-amylase activity using a maltooligosaccharide derivative as a substrate. The reaction is carried out, for example, at 25°–40° C. and pH 6–8 for about 1 to 20minutes.

When aglycone shows a change in absorbance upon cleavage by α-amylase, the change in absorbance is measured. When aglycone shows a change in fluorescence upon cleavage, the change in fluorescence is measured. For example, when aglycone is 2-chloro-4-nitrophenol, a change in the absorbance at around 400 nm is measured.

The reaction scheme of the substrate decomposition in the determination of α-amylase activity according to the method of the present invention is shown in the following by referring to 2-chloro-4-nitrophenyl 4-O-β-D-galactopyranosyl-α-maltoside as a substrate. As shown in the following reaction formulas, adjuvant enzyme is not necessary, since the substrate is directly decomposed by α-amylase.

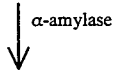

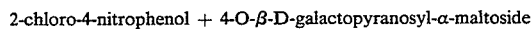

Measurement, by a suitable means, of the aglycone portion liberated by the aforementioned reaction permits determination of α-amylase activity. In the example given above, absorption spectrum of the liberated 2-chloro-4-nitrophenol is directly measured. The method for measuring 2-chloro-4-nitrophenol includes, for example, rate assay in which the reaction of α-amylase is continuously monitored, and end point assay in which measurement is performed upon termination of a certain period of reaction.

The reagent for determining α-amylase activity of the present invention is not confined to the use for determining α-amylase in a body fluid but is also applicable to determination of calcium ion or chloride ion in a sample, which is conducted via determination of α-amylase activity.

The reagent of the present invention does not require use of any adjuvant enzyme such as α-glucosidase, β-glucosidase, or glucoamylase, and is stable since the substrate is not exposed to the decomposition by the aforesaid adjuvant enzymes. The substrate used in the present invention has high affinity for α-amylase. Thus, the reagent and the determination method of the present invention make it possible to determine α-amylase activity with high sensitivity.

The substrate to be used in the present invention has galactopyranosyl as a modifying group for non-reducing terminal, which assumedly faithfully reflects the action mode of α-amylase, whereby glucose chains of starch or amylose are recognized and their bonds are cleaved.

The present invention is detailedly explained in the following by illustrating examples, to which the invention is by no means limited.

EXAMPLE

For Examples, the reagents for determining α-amylase activity having the following composition were respectively prepared by using the substrates indicated in Table 1 to be given below (Example A and Example B).

REAGENT COMPOSITION 50 mM Good buffer (pH 7.0)
$CaCl_2$ 1 mM
Substrate 2 mM

For Comparative Examples, the reagents similar to the above-mentioned were prepared by using the substrates indicated in Table 1 to be given below (Comparative Example A-1, Comparative Example A-2, Comparative Example B-1, Comparative Example B-2).

TABLE 1

| | Substrate |
|---|---|
| Example A | 2-chloro-4-nitrophenyl 4-O-β-D-galactopyranosyl-α-maltoside |
| Comparative Example A-1 | 3-ketobutylidene 2-chloro-4-nitrophenyl-α-maltoside |

TABLE 1-continued

| | Substrate |
|---|---|
| Comparative Example A-2 | 2-chloro-4-nitrophenyl α-maltotrioside |
| Example B | p-nitrophenyl 4-O-β-D-galactopyranosyl-α-maltoside |
| Comparative Example B-1 | 3-ketobutylidene p-nitrophenyl-α-maltoside |
| Comparative Example B-2 | p-nitrophenyl α-maltotrioside |

EXPERIMENTAL EXAMPLE

Determination of α-amylase activity

Three kinds of sera 1, 2, and 3 (0.25 ml each) were respectively added to each reagent (3 ml) prepared in the aforementioned Examples and Comparative Examples, and the mixtures were left standing at 37° for 3 minutes. Then, changes in absorbance at 415 nm were measured, based on which changes in absorbance per minute were calculated. The results are shown in Table 2 which also indicates changes in absorbance per minute of blank sample.

TABLE 2

| | Changes in absorbance per minute | | | |
|---|---|---|---|---|
| | Serum 1 | Serum 2 | Serum 3 | Blank sample |
| Example A | 0.0208 | 0.0226 | 0.0444 | 0.0017 |
| Comp.Ex.A-1 | 0.0128 | 0.0139 | 0.0224 | 0.0027 |
| Comp.Ex.A-2 | 0.0134 | 0.0147 | 0.0289 | 0.0024 |
| Example B | 0.0108 | 0.0119 | 0.0231 | 0.0007 |
| Comp.Ex.B-1 | 0.0049 | 0.0054 | 0.0105 | 0.0009 |
| Comp.Ex.B-2 | 0.0066 | 0.0073 | 0.0142 | 0.0012 |

As shown in Table 2, comparison of the results of Example A and Comparative Example A-1, and comparison of the results of Example B and Comparative Example B-1 respectively show that β-galactopyranosyl is superior in affinity for α-amylase and therefore preferable as a modifying group for the non-reducing terminal.

In addition, comparison of the results of Example A and Comparative Examples A-1, A-2 and comparison of the results of Example B and Comparative Examples B-1, B-2 respectively show that the reagent of the invention has high determination sensitivity.

What is claimed is:

1. A reagent for determining α-amylase activity, comprising a maltooligosaccharide derivative of the following formula

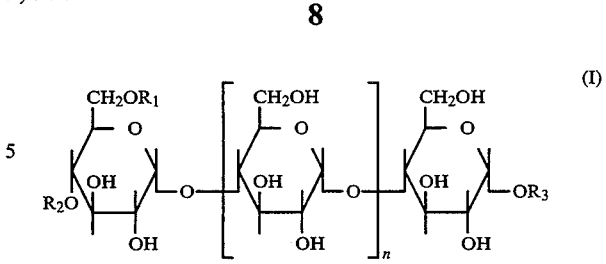

(I)

(wherein either one of $R_1$ and $R_2$ is β-galactopyranosyl and the other is hydrogen, $R_3$ is a group bonded to the reducing terminal glucose via a bond cleavable by α-amylase, which becomes a measurable substance upon cleavage of said bond, and n is an integer of 0–2), which does not comprise adjuvant enzymes.

2. The reagent of claim 1 further comprising a buffer.

3. The reagent of claim 1 wherein n is 0.

4. The reagent of claim 1, wherein the maltooligosaccharide derivative is a compound of the formula

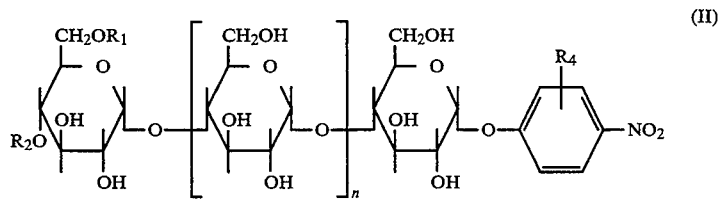

(II)

wherein $R_1$ and $R_2$ are as defined in claim 1, $R_4$ is hydrogen or a substituent selected from the group consisting of halogen, alkyl having 1 to 6 carbon atoms, —$OR_5$, and —$COOR_5$ ($R_5$ is alkyl having 1 to 6 carbon atoms), and n is an integer of 0–2.

5. The reagent of claim 4 wherein n is 0.

6. The reagent of claim 4 wherein the maltooligosaccharide derivative is selected from the group consisting of 2-chloro-4-nitrophenyl 4-O-β-D-galactopyranosyl-α-maltoside, p-nitrophenyl 4-O-β-D-galactopyranosyl-α-maltoside, 2-chloro-4-nitrophenyl 4-O-β-D-galactopyranosyl-α-maltotrioside, p-nitrophenyl 4-O-β-D-galactopyranosyl-α-maltotrioside, 2-chloro-4-nitrophenyl 4-O-β-D-galactopyranosyl-α-maltotetraoside, and p-nitrophenyl 4-O-β-D-galactopyranosyl-α-maltotetraoside.

7. The reagent of claim 6 wherein the maltooligosaccharide derivative is 2-chloro-4-nitrophenyl 4-O-β-D-galacto-pyranosyl-α-maltoside.

8. The reagent of claim 6 wherein the maltooligosaccharide derivative is p-nitrophenyl 4-O-β-D-galactopyranosyl-α-maltoside.

9. A method for determining α-amylase activity in a sample, which comprises the steps of
(a) contacting a sample containing α-amylase with a maltooligosaccharide derivative of the formula

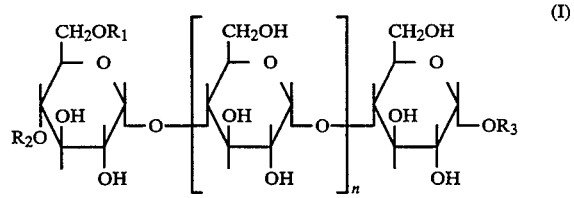

(I)

(wherein either one of $R_1$ and $R_2$ is β-galactopyranosyl and the other is hydrogen, $R_3$ is a group bonded to the reducing terminal glucose via a bond cleavable by α-amylase, and which becomes a measurable substance upon cleavage of the bond, and n is an integer of 0–2), in the absence of adjuvant enzyme to cause a reaction of the maltooligosaccharide derivative with α-amylase; and
  (b) measuring the amount of the liberated measurable substance.

10. The method of claim 9, wherein n is 0.

11. The method of claim 9, wherein the maltooligosaccharide derivative is a compound of the formula

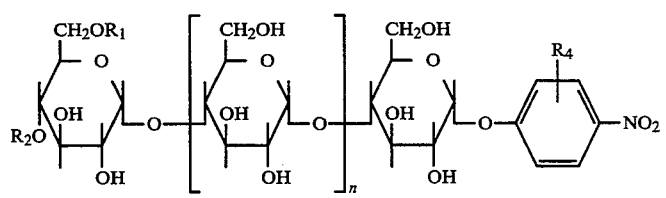

(II)

wherein $R_1$ and $R_2$ are as defined in claim 9, $R_4$ is hydrogen or a substituent selected from the group consisting of halogen, alkyl having 1 to 6 carbon atoms, —$OR_5$, and —$COOR_5$ ($R_5$ is alkyl having 1 to 6 carbon atoms), and n is an integer of 0–2.

12. The method of claim 11 wherein n is 0.

13. The method of claim 11 wherein the maltooligosaccharide derivative is a compound selected from the group consisting of 2-chloro-4-nitrophenyl 4-O-β-D-galactopyranosyl-α-maltoside, p-nitrophenyl 4-O-β-D-galactopyranosyl-α-maltoside, 2-chloro-4-nitrophenyl 4-O-β-D-galactopyranosyl-α-maltotrioside, p-nitrophenyl 4-O-β-D-galactopyranosyl-α-maltotrioside, 2-chloro-4-nitrophenyl 4-O-β-D-galactopyranosyl-α-maltotetraoside, and p-nitrophenyl 4-O-β-D-galacto-pyranosyl-α-maltotetraoside.

14. The method of claim 13 wherein the maltooligosaccharide derivative is 2-chloro-4-nitrophenyl 4-O-β-D-galactopyranosyl-α-maltoside.

15. The method of claim 13 wherein the maltooligosaccharide derivative is p-nitrophenyl 4-O-β-D-galactopyranosyl-α-maltoside.

* * * * *

UNITED STATES PATENT AND TRADEMARK OFFICE
CERTIFICATE OF CORRECTION

PATENT NO. : 5,393,660
DATED : FEBRUARY 28, 1995
INVENTOR(S) : SUMIO KITAHATA, NOBUHIRO KUWAHARA, KOKI FUJITA, KOJI HARA, KEIICHI MAJIMA, SHIN-ICHI TESHIMA AND YUZO HAYASHI

It is certified that error appears in the above-indentified patent and that said Letters Patent is hereby corrected as shown below:

Column 5, line 13, delete "arthydride" and substitute therefor -- anhydride --; and Column 7, line 18, after "37°" insert -- C. --.

Signed and Sealed this

Fifth Day of September, 1995

Attest:

Attesting Officer

BRUCE LEHMAN

Commissioner of Patents and Trademarks

UNITED STATES PATENT AND TRADEMARK OFFICE
CERTIFICATE OF CORRECTION

PATENT NO. : 5,393,660

DATED : FEBRUARY 28, 1995

INVENTOR(S) : SUMIO KITAHATA, NOBUHIRO KUWAHARA, KOKI FUJITA, KOJI HARA, KEIICHI MAJIMA, SHIN-ICHI TESHIMA AND YUZO HAYASHI

It is certified that error appears in the above-indentified patent and that said Letters Patent is hereby corrected as shown below:

ON THE TITLE PAGE:

[73] Assignees: after "Toyo Boseki Kabushiki Kaisha, Osaka;" insert -- Osaka Municipal Government, Osaka --; and after "Kanagawa" delete "both" and substitute therefor -- all --; and Signed and Sealed this Fourteenth Day of November, 1995

Attest:

BRUCE LEHMAN

Attesting Officer

Commissioner of Patents and Trademarks